(12) United States Patent
Harvey (10) Patent No.: US 7,464,614 B2
(45) Date of Patent: Dec. 16, 2008

(54) OFFLINE SOLID PHASE MICROEXTRACTION SAMPLING SYSTEM

(75) Inventor: Chris A. Harvey, French Camp, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 2 days.

(21) Appl. No.: 11/437,906

(22) Filed: May 18, 2006

(65) Prior Publication Data

US 2006/0260419 A1 Nov. 23, 2006

Related U.S. Application Data

(60) Provisional application No. 60/682,729, filed on May 18, 2005.

(51) Int. Cl.
 *G01N 1/10* (2006.01)
(52) U.S. Cl. ............... 73/863.84; 73/863.85; 73/863.86
(58) Field of Classification Search . 73/863.81–863.86, 73/863.71
See application file for complete search history.

(56) References Cited

U.S. PATENT DOCUMENTS

| | | | |
|---|---|---|---|
| 5,431,067 A * | 7/1995 | Anderson et al. | 73/863.86 |
| 5,747,708 A * | 5/1998 | Weiberth | 73/863.81 |
| 6,164,144 A | 12/2000 | Berg | |
| 6,354,135 B1 | 3/2002 | McGee et al. | |
| 6,708,550 B2 | 3/2004 | McGee et al. | |
| 6,759,126 B1 | 7/2004 | Mulik et al. | |
| 6,783,680 B2 | 8/2004 | Malik | |
| 6,825,046 B1 | 11/2004 | Forsyth | |
| 2002/0182746 A1 * | 12/2002 | Mester et al. | 436/178 |
| 2007/0172960 A1 * | 7/2007 | Malik et al. | 436/161 |

OTHER PUBLICATIONS

Chris A. Harvey et al, Offline Solid Phase MicroExtraction (SPME) IM-320937-1; Jun. 16, 2005 pp. 1-14.

* cited by examiner

*Primary Examiner*—Hezron Williams
*Assistant Examiner*—Nashmiya S Fayyaz
(74) *Attorney, Agent, or Firm*—James S. Tak; John H. Lee (57) ABSTRACT

An offline solid phase microextraction (SPME) sampling apparatus for enabling SPME samples to be taken a number of times from a previously collected fluid sample (e.g. sample atmosphere) stored in a fused silica lined bottle which keeps volatile organics in the fluid sample stable for weeks at a time. The offline SPME sampling apparatus has a hollow body surrounding a sampling chamber, with multiple ports through which a portion of a previously collected fluid sample may be (a) released into the sampling chamber, (b) SPME sampled to collect analytes for subsequent GC analysis, and (c) flushed/purged using a fluidically connected vacuum source and purging fluid source to prepare the sampling chamber for additional SPME samplings of the same original fluid sample, such as may have been collected in situ from a headspace.

25 Claims, 5 Drawing Sheets

OFFLINE SOLID PHASE MICROEXTRACTION SAMPLING SYSTEM

I. CLAIM OF PRIORITY IN PROVISIONAL APPLICATION

This application claims priority in provisional application No. 60/682,729, filed on May 18, 2005, entitled "Offline Solid Phase Microextraction (SPME) Sampling System" by Chris A. Harvey.

The United States Government has rights in this invention pursuant to Contract No. W-7405-ENG-48 between the United States Department of Energy and the University of California for the operation of Lawrence Livermore National Laboratory.

II. FIELD OF THE INVENTION

The present invention relates to solid phase microextraction (SPME) sampling, and more particularly to an offline SPME sampling apparatus, system, and process that enables multiple samplings of a fluid sampled from a sampling environment, such as a headspace, without loss of the original fluid sample composition.

III. BACKGROUND OF THE INVENTION

Solid phase micro-extraction (SPME) is a common sampling technique which uses a syringe-like sample collection device to perform analyte collection, concentration, and separation without the use of solvents or the need for exhaustive extractions. Such SPME collection devices have an active portion usually consisting of a fused silica fiber coated with an active absorbent or media. The coated SPME fiber is typically housed in the needle (used for piercing a septum) of the syringe-like SPME device, and can be mechanically extended/retracted. In the SPME sampling process, a SPME fiber is introduced into a fluid carrier/sampling environment in the field (e.g. sampling atmosphere, volume, or space, such as a headspace) so that the SPME fiber is exposed to trace analytes (e.g. volatile organics) in the sampling environment and adsorbs and concentrates the analytes on the polymer coating. Exposed fiber is then inserted into a gas chromatagraph (GC) where the collected analytes are desorbed and separated, and a mass spectrometer provides spectral information of the analytes detailing their chemical composition.

However, traditional SPME sampling is limited by the fact that it is traditionally a "one shot" technique, where a sample extracted from a sampling environment using a SPME fiber/device is used up in the desorbtion/analysis step such that additional analysis cannot be performed with the same SPME fiber/device without re-sampling the sampling environment in the field. By the time another SPME extraction can be done, however, the sampling environment can be changed or altered or may be totally unavailable or dissipated. As such, quantitation of the sample environment may be limited. Moreover, the reliance on a single exposed SPME fiber as the representative measure of a sampling atmosphere may be unduly risking because of the fragile nature of SPME fiber and the potential loss of data results due to fiber damage or contamination. And furthermore, a single fiber type may not collect all analytes of interest. Thus, it can be seen that "one shot" sampling results are subject to many factors that may limit or completely eliminate useable data.

What is needed therefore is a SPME sampling apparatus and procedure that will eliminate the "one shot" problems associated with traditional SPME sampling and analysis by enabling fluid samples (e.g. sample atmospheres from a headspace) to be sub sampled and held stable for weeks at a time, during which time organic constituents are kept stable from breakdown. Furthermore, such a SPME sampling apparatus and procedure would enable multiple samplings of the sample atmosphere without a loss of the original sample atmosphere composition.

IV. SUMMARY OF THE INVENTION

One aspect of the present invention includes an offline solid phase microextraction (SPME) sampling apparatus, comprising: a hollow body surrounding a sampling chamber; a first port of said hollow body having a first port connector capable of fluidically connecting a fluid sample container to said first port so as to enable controlled fluidic communication with said sampling chamber; a second port of said hollow body having a septum capable of being pierced by a SPME needle/fiber therethrough for sampling said sampling chamber thereby; means for fluidically connecting a vacuum source and a purging fluid source to said hollow body; and valve means for controlling fluidic communication between a connected vacuum source and said sampling chamber and between a connected purging fluid source and said sampling chamber.

Another aspect of the present invention includes an offline solid phase microextraction (SPME) sampling system, comprising: a vacuum source; a purging fluid source; a hollow body surrounding a sampling chamber; a first port of said hollow body having a first port connector capable of fluidically connecting a fluid sample container to said first port so as to enable controlled fluidic communication with said sampling chamber; a second port of said hollow body having a septum capable of being pierced by a SPME needle/fiber therethrough for sampling said sampling chamber thereby; means for fluidically connecting said vacuum source and said purging fluid source to said hollow body; and valve means for controlling fluidic communication between said vacuum source and said sampling chamber and between said purging fluid source and said sampling chamber.

Another aspect of the present invention includes an offline solid phase microextraction (SPME) sampling process comprising: providing an offline SPME sampling system comprising: a vacuum source; a purging fluid source; a hollow body surrounding a sampling chamber; a first port of said hollow body having a first port connector capable of fluidically connecting a fluid sample container to said first port, said fluid sample container having an integrated valve for controlling the fluidic communication between said connected fluid sample container and said sampling chamber; a second port of said hollow body having a septum capable of receiving a SPME needle/fiber therethrough for sampling said sampling chamber thereby; means for fluidically connecting said vacuum source and said purging fluid source to said hollow body; and valve means for controlling fluidic communication between said vacuum source and said sampling chamber and between said purging fluid source and said sampling chamber; capturing a fluid sample in a fluid sample container having an integrated valve; connecting the fluid sample container to said first port; controlling the integrated valve of said connnected fluid sample container to release a portion of the fluid sample therefrom and into the sampling chamber; inserting a SPME needle/fiber through the septum of the second port and SPME sampling the fluid sample in the sampling chamber; removing the SPME needle/fiber from the second port; and purging and flushing the fluid sample from the sampling chamber.

Another aspect of the present invention includes an offline solid phase microextraction (SPME) sampling process comprising: providing an offline SPME sampling system comprising: a vacuum source; a purging fluid source; a hollow body surrounding a sampling chamber; a first port of said hollow body having a first port connector capable of fluidically connecting a fluid sample container to said first port and a first port valve for controlling fluidic communication between a connected fluid sample container and said sampling chamber; a second port of said hollow body having a septum capable of receiving a SPME needle/fiber therethrough for sampling said sampling chamber thereby; means for fluidically connecting said vacuum source and said purging fluid source to said hollow body; and valve means for controlling fluidic communication between said vacuum source and said sampling chamber and between said purging fluid source and said sampling chamber; capturing a fluid sample in a fluid sample container; connecting the fluid sample container to said first port; controlling said first port valve to release a portion of the fluid sample from the fluid sample container into the sampling chamber; inserting a SPME needle/fiber through the septum of the second port and SPME sampling the fluid sample in the sampling chamber; removing the SPME needle/fiber from the second port; and purging and flushing the fluid sample from the sampling chamber.

Another aspect of the present invention includes an offline solid phase microextraction (SPME) sampling process comprising: providing an offline SPME sampling system comprising: a hollow body surrounding a sampling chamber; a first port of said hollow body having a first port connector capable of interchangeably fluidically connecting a fluid sample container, a vacuum source, and a purging gas source to said first port, and a first port valve for interchangeably controlling fluidic communication between said sampling chamber and a fluid sample container, a vacuum source, and a purging gas source; a second port of said hollow body having a septum capable of receiving a SPME needle/fiber therethrough for sampling said sampling chamber thereby; capturing a fluid sample in a fluid sample container; fluidically connecting the fluid sample container to said first port; controlling said first port valve to release a portion of the fluid sample from the fluid sample container into the sampling chamber; inserting a SPME needle/fiber through the septum of the second port and SPME sampling the fluid sample in the sampling chamber; removing the SPME needle/fiber from the second port; disconnecting the fluid sample container form said first port; fluidically connecting said first port to a purging gas source and vacuum source; and purging and flushing the fluid sample from the sampling chamber.

V. BRIEF DESCRIPTION OF THE DRAWINGS

The accompanying drawings, which are incorporated into and form a part of the disclosure, are as follows.

VI. DETAILED DESCRIPTION

Generally, the apparatus of the present invention may be characterized as a fluidic hub surrounding a sampling chamber which is in fluidic communication with multiple ports through which a portion of a previously collected fluid sample may be (a) released into the sampling chamber, (b) SPME sampled to collect analytes for subsequent GC analysis, and (c) flushed/purged to prepare the sampling chamber for additional SPME samplings of the same previously collected fluid sample. In this manner, multiple SPME sampling runs may be performed for each original in situ collected fluid sample without total loss of the original fluid sample or changes to its initial organic composition since only a small amount of the original fluid sample is required for each SPME sampling and subsequent GC analysis. Additionally, the present invention enables time/place shifting of the SPME sampling in an "offline" SPME process which is removed in time and place from the actual sampling environment. This is different form the traditional "inline" SPME process in which analytes are sampled and collected directly from the field sampling environment with a syringe-line SPME device for subsequent desorbtion/analysis in a GC. This serves to limit access time to the sampling environment to only what is necessary to acquire the original fluid sample, and enables a significant reduction of downtime of critical sampling environments, such as for example the headspace of weapons bays. Furthermore, by performing SPME sampling offline and away from the in situ sampling environment, the syringe-line SPME devices are no longer subject to fiber breakage or instrument failure. Also, quantitation options may be expanded since surrogates and internal standards can be added. And multiple SPME runs can be performed using different fibers to generate additional information.

Figure 1:
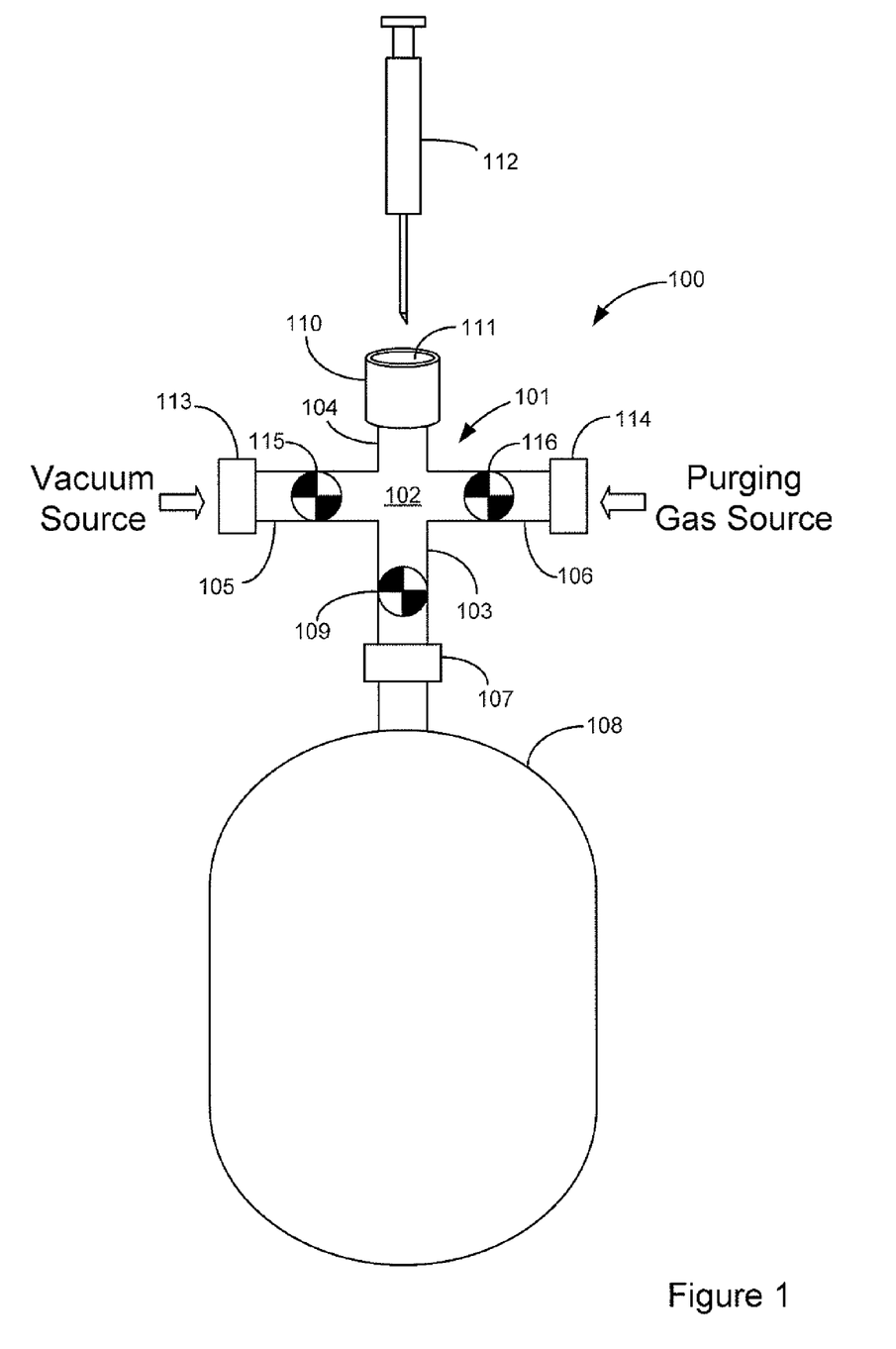
FIG. 1 is a schematic view a first exemplary embodiment of the SPME sampling apparatus of the present invention, shown with a connected fused silica lined fluid container.

Turning now to the drawings, FIG. 1 shows a first exemplary embodiment of the offline SPME sampling apparatus of the present invention, generally indicated at reference character 100. The apparatus has a rigid hollow body 101 surrounding a sampling chamber 102 and with multiple ports 103-106 in fluidic communication with the sampling chamber. Preferred materials include various metals and alloys, such as for example steel, brass, etc. FIG. 1 shows in particular a "cross" configuration of the hollow body where all ports intersect at the centrally located sampling chamber 102. It is appreciated however that other configurations and arrangements are possible to enhance flows through the sampling chamber (see for example the T-configuration of FIG. 3).

In any case a first port 103 is shown having a connector 107 which is adapted to fluidically connect a fluid sample container, such as 108, to the first port. The connector may be any type known in the art for making a controlled fluidic connection. Preferably, the fluid sample container is a fused silica lined fluid container, and in particular a fused silica lined gas bottle, i.e. a bottle with a SPME layer lining the inner surface. Such fused silica lined bottles provide long shelf life of a fluid sample by holding organic compounds over longer periods of time (e.g. weeks at a time) without degradation. Various types are commercially available. As in the case of typical SPME collection devices, the absorbing material can be a wide variety of organic or inorganic materials, with some examples of commercially available media including polydimethyl siloxane (PDMS), bonded divinylbenzene/styrene spheres, activated carbon spheres, etc. Fluid flow between the fused silica lined fluid container 108 and the sampling chamber 102 may be controlled with a valve 109, shown generically. It is appreciated that various types of valves may be employed, including a manual type screw valve, or quick connect type valves which may be operated simply by the act of connecting or disconnecting the connectors. Additionally various sizes of fused silica lined fluid containers may be employed, such as for example from 10 ml to 15 liters.

A second port 104 is also shown having a septum 111 at one end which may be pierced by a SPME needle/fiber of a SPME collection device 112 to enter the sampling chamber 102 where SPME sampling may be performed. Standard septums are often non-resealing, and must be replaced after each use. In this case the septum may be provided as a septum nut 110 having for example internal threads to connect to an externally threaded first port of the hollow body, for facilitating the installation and removal of new septums after each use. In an alternative embodiment the septum is preferably a reuseable type, such as for example, a Merlin™ microseal which is capable of resealing for repeated insertions.

Also shown in FIG. 1 are a third port 105 and a fourth port 106. These ports enable fluidic connection and communication with a vacuum source and a purging gas source, respectively, which are used to prepare the sampling chamber 102 for SPME sampling by purging the chamber of any particulates/contaminants such as may be remaining from a previous SPME sampling. A connector 113 is shown for fluidically connecting to a vacuum source and a connector 114 is shown for fluidically connecting to a purging gas source. A preferred purging gas used in an exemplary embodiment is nitrogen gas. Similar to the first port connector 207, various types of connectors and fittings may be employed here as well for connectors 113 and 114. Conventional fittings may be used, such as for example VCR4, Swagelok fittings, etc. Flow control devices, such as valves 115 and 116 are also shown in FIG. 1 for flush/filling the sampling chamber prior to and after each SPME fiber sampling of the sampling chamber. In particular, valve 115 is used to control fluid flow between the vacuum source and the sampling chamber 102, and valve 114 is used to control fluid flow between the purging gas source and the sampling chamber 102. The "cross" configuration shown in FIG. 1 may serve to streamline the purging contaminants from the sampling chamber due to the relative locations of the third port 105 and the fourth port 106 on opposite ends of the sampling chamber 102.

Operation of a SPME sampling process using the first exemplary embodiment of FIG. 1 would involve capturing a fluid sample in situ from a field sampling environment using known methods of fluid sample capture. As previously discussed, the use of a fused silica (SPME) lined fluid container enables the storage of a fluid sample and its volatile analytes for extended periods of time, such as for example several weeks. Once captured, the fluid container is fluidically connected to the first port 103 via connector 107 and a small portion of the fluid sample in the fluid container is released into the sampling chamber 102. A SPME collection device such as 112 is then inserted into the sampling chamber by piercing the septum 111 and SPME sampling is performed. When completed, the sampling chamber may be purged by filling the sampling chamber with purging gas and evacuating/flushing the sampling chamber via the vacuum source. In this manner, multiple SPME samplings may be performed using the same, non-degraded original fluid sample contained in the fluid container 108.

Figure 2:
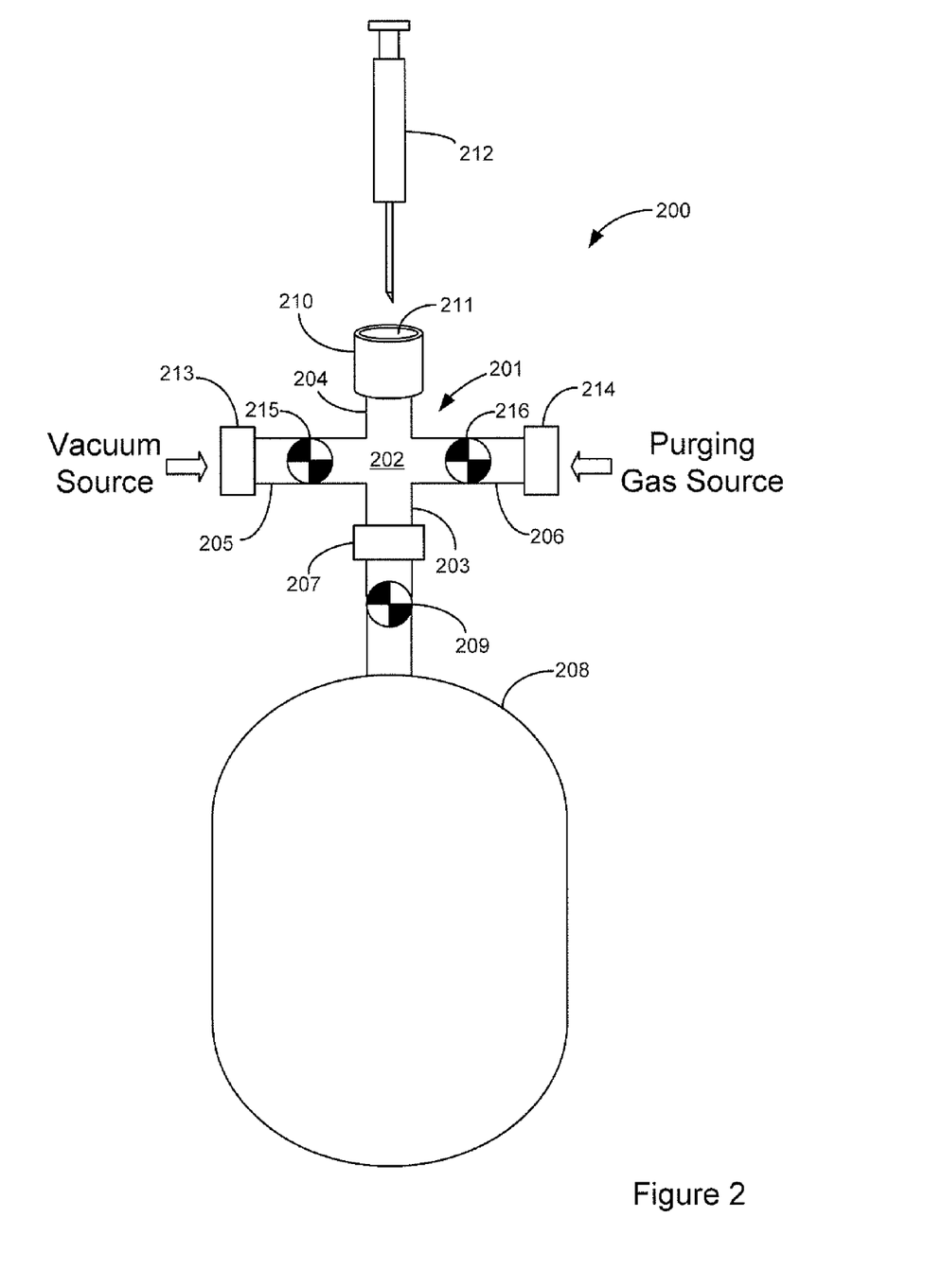
FIG. 2 is a schematic view a second exemplary embodiment of the offline SPME sampling apparatus of the present invention, shown with a connected fused silica lined fluid container having an integrated valve.

FIG. 2 shows a second exemplary embodiment of the SPME sampling apparatus of the present invention, generally indicated at 200 which is similar in may respects to the first exemplary embodiment 100. The second embodiment 200 also has a rigid hollow body 201 surrounding a sampling chamber 202 and with multiple ports 203-206 in fluidic communication with the sampling chamber. FIG. 2 also shows in particular a "cross" configuration of the hollow body where all ports intersect at the centrally located sampling chamber 202. The hollow body 201 also has a second port 204 having a septum 211 at one end which may be pierced by a SPME needle/fiber of a SPME collection device 112 to enter the sampling chamber 202 where SPME sampling may be performed. As before, the septum may be provided as a septum nut 210 for facilitating the installation and removal of new septums after each use. Reuseable alternatives also include for example, a Merlin™ microseal which is capable of resealing for repeated insertions. The second embodiment also includes a third port 205 and a fourth port 206, which enable fluidic connection and communication with a vacuum source and a purging gas source, respectively. A connector 213 is shown for fluidically connecting to a vacuum source and a connector 214 is shown for fluidically connecting to a purging gas source. And flow control devices, such as valves 215 and 216 are also shown in FIG. 2 for flush/filling the sampling chamber prior to and after each SPME fiber sampling of the sampling chamber.

The difference between the first and second embodiments can be seen in that the hollow body 201 has a first port 203 having a connector 207 but not a flow control device. In this second embodiment, an integrated valve is found as part of the fused silica lined fluid container 208. It is appreciated that the connector 207 in this case is adapted to fluidically connect to such a fluid sample container, and includes means for sealing the port 203 when a container is not connected. As previously discussed this can be achieved using a quick connect type fitting known in the art. Thus, fluid flow between the fused silica lined fluid container 208 and the sampling chamber 202 may be controlled with the container's integrated valve 209.

Figure 3:
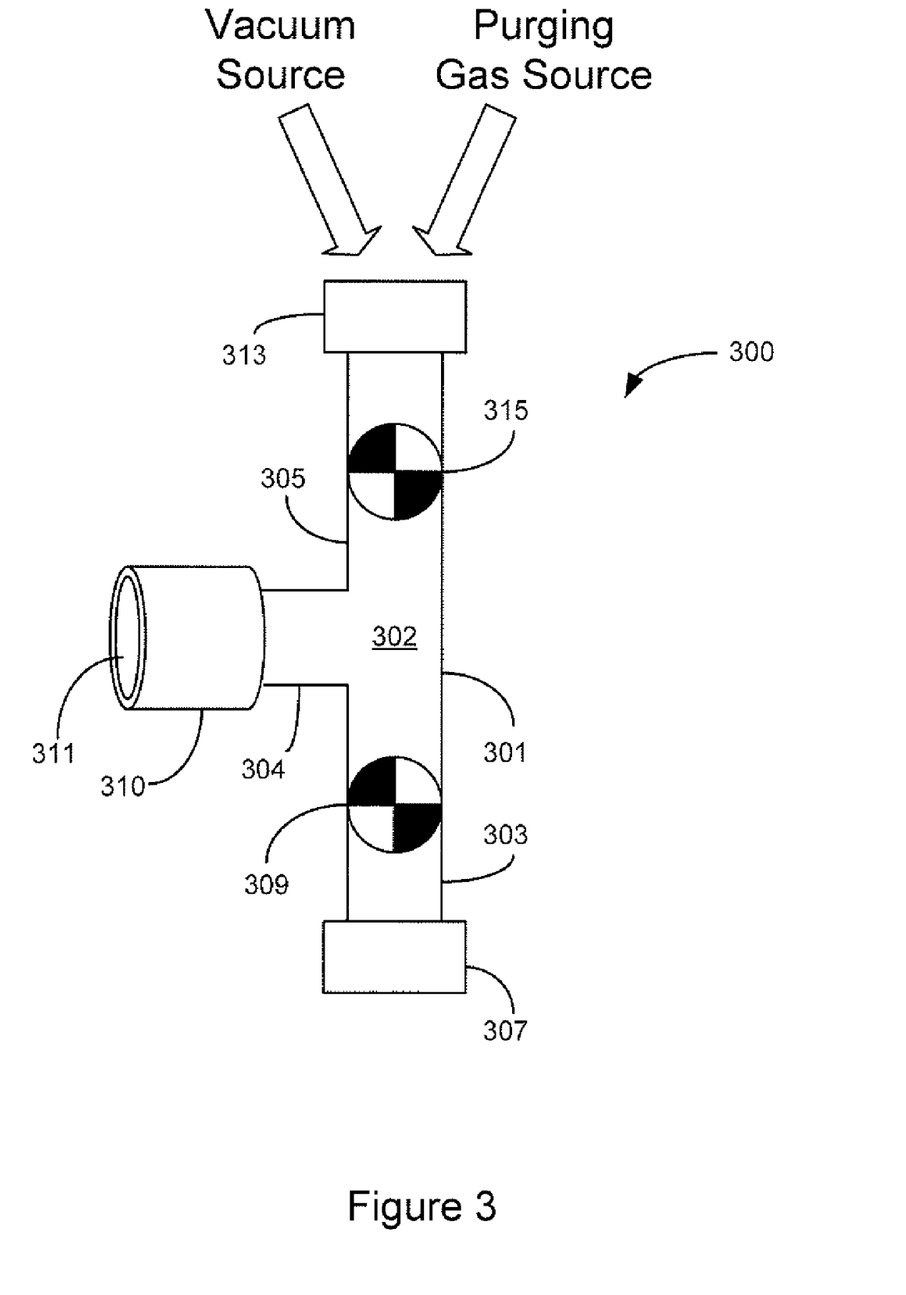
FIG. 3 is a schematic view of a third exemplary embodiment of the offline SPME sampling apparatus of the present invention having a T-configuration.

FIG. 3 shows a third exemplary embodiment of the SPME sampling apparatus of the present invention, generally indicated at 300, having a T-configuration. As in previous embodiments, it includes a hollow body 301 surrounding a sampling chamber 302, and having a first port 303 with a connector 307 and a valve 309 for connecting to and controlling fluid flow between a fused silica lined container (not shown) and the sampling chamber 302. It also includes a second port 304 having a septum 311 preferably provided on a septum nut 310. However, the third port 305 of the T-configuration is capable of fluidically connecting to both a vacuum source and a purging gas source. This may be accomplished, for example, by using a splitter (not shown) which connects to connector 313. Valve 315 then controls either the filling of the sampling chamber with purging gas, or the evacuation/purging of the chamber. It is appreciated that the valve may be a switch type valve which opens fluidic communication with one of the sources while closing off fluidic communication with the other.

Figure 4:
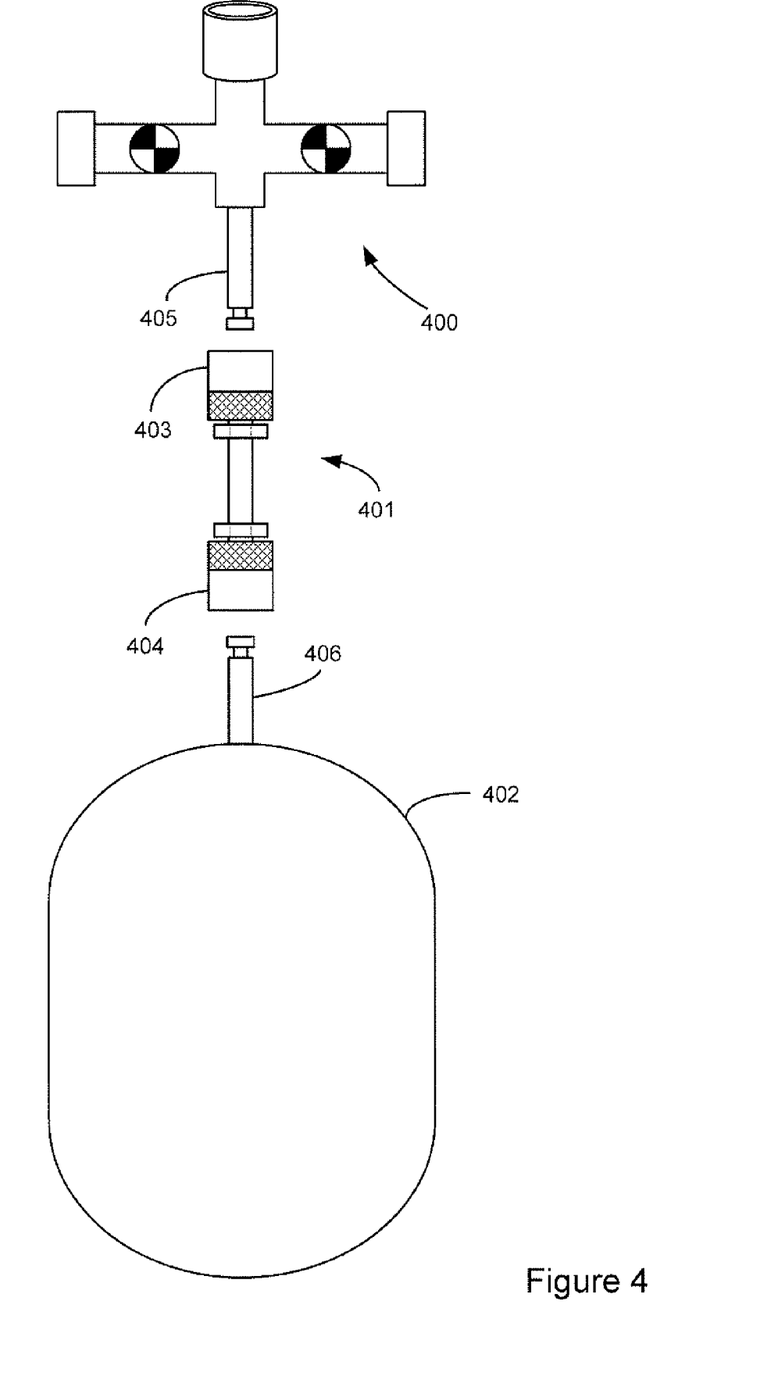
FIG. 4 is a schematic view of a fourth exemplary embodiment of the offline SPME sampling apparatus of the present invention using a quick connect mechanism for quickly connecting/disconnecting a fused silica lined fluid container.

An FIG. 4 shows a fourth exemplary embodiment of the SPME sampling apparatus of the present invention, generally indicated at 400, having a quick-connect type connector 405 which automatically opens or closes fluidic communication with the sampling chamber based on whether an independent connector piece, such as adaptor 401 is connected thereon. Adaptor 401 is used in this embodiment having a mating connector on either end, with the connector 403 adapted to mate with and open fluidic communication when connected to connector 405 of the apparatus 400, and the connector 404 adapted to mate with and open fluidic communication when connected to connector 406 of the fused silica lined fluid container 402. Similar to the connector 405 of the apparatus the connector 406 of the container is also a quick-connect type connector which automatically opens or closes at connection/disconnection.

Figure 5:
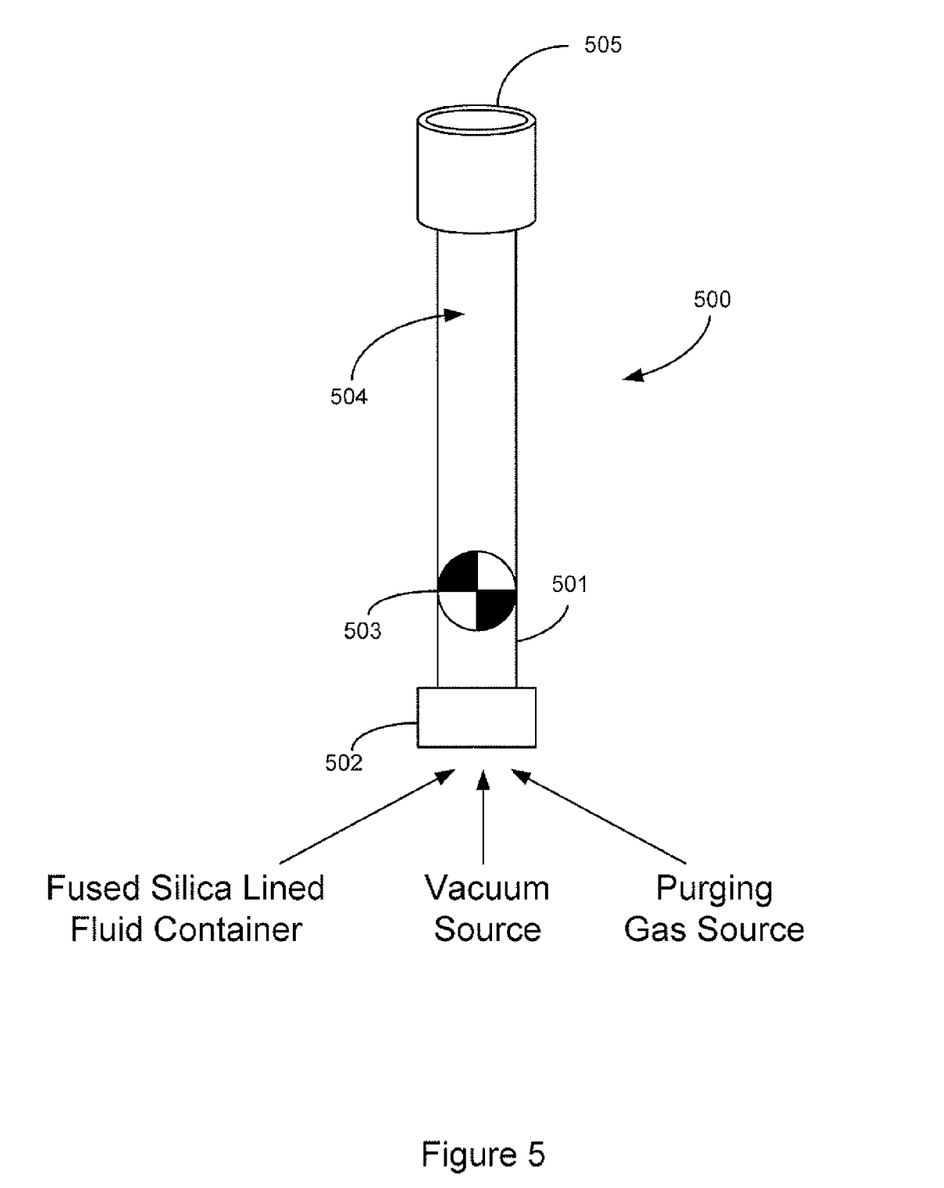
FIG. 5 is a schematic view of a fifth exemplary embodiment of the offline SPME sampling apparatus of the present invention using a single port to fluidic connect to (a) a fused silica lined fluid container, (b) a vacuum source, and (c) a purging gas source.

FIG. 5 is a schematic view of a fifth exemplary embodiment of the offline SPME sampling apparatus of the present invention 500, using a single port 501 to interchangeably and fluidically connect to (a) a fused silica lined fluid container, (b) a vacuum source; and (c) a purging gas source, via connector 502. A valve 503 is shown separate from connector 502, however, it is appreciated that the valve and connector may be integrated together, such as in a quick connect type connector/valve. Operation using this embodiment would involve fluidically connecting a fused silica lined container (not shown) to the connector 502, releasing a small portion of a capture sample fluid into a sampling chamber 504, inserting a SPME sampling device through septum 505, disconnecting the fluid container and connecting a vacuum source and/or purging gas source (not shown) to the connector 502. And purging/flushing the sampling chamber to prepare the sampling chamber for additional SPME samplings.

While particular operational sequences, materials, temperatures, parameters, and particular embodiments have been described and or illustrated, such are not intended to be limiting. Modifications and changes may become apparent to those skilled in the art, and it is intended that the invention be limited only by the scope of the appended claims.

I claim:

1. An offline solid phase microextraction (SPME) sampling apparatus, comprising:
   a hollow body surrounding a sampling chamber;
   a first port of said hollow body having a first port connector adapted to physically and fluidically interconnect an access port of a fluid sample container to said first port so as to enable controlled fluidic communication with said sampling chamber;
   a second port of said hollow body having a septum capable of being pierced by a SPME needle/fiber therethrough for sampling said sampling chamber thereby;
   means for fluidically connecting a vacuum source and a purging fluid source to said hollow body; and
   valve means for controlling fluidic communication between the connected vacuum source and said sampling chamber and between the connected purging fluid source and said sampling chamber.

2. The apparatus of claim 1,
   wherein said first port has a first port valve for controlling the fluidic communication between the connected fluid sample container and said sampling chamber.

3. The apparatus of claim 1,
   wherein said first port connector is capable of fluidically connecting a fluid sample container of a type having an integrated valve for controlling the fluidic communication between the connected fluid sample container and said sampling chamber.

4. The apparatus of claim 1,
   wherein said means for fluidically connecting and said valve means for controlling fluidic communication first port are integrated as part of said first port connector so as to interchangeably enable fluidic communication between said sampling chamber and each of said fluid sample container, the vacuum source, and the purging gas source.

5. The apparatus of claim 1,
   further comprising third and fourth ports of said hollow body, and
   wherein said means for fluidically connecting comprises a third port connector capable of fluidically connecting the vacuum source to said third port, and a fourth port connector capable of fluidically connecting the purging fluid source to said fourth port; and said valve means comprises a third port valve for controlling fluidic communication between the connected vacuum source and said sampling chamber via said third port, and a fourth port valve for controlling fluidic communication between the connected purging fluid source and said sampling chamber via said fourth port.

6. The apparatus of claim 5,
   wherein said third port and said fourth port are on opposite sides of said hollow body.

7. The apparatus of claim 1,
   further comprising a third port of said hollow body, and
   wherein said means for fluidically connecting comprises a third port connector capable of fluidically connecting the vacuum source and the purging fluid source to said third port; and said valve means comprises a third port valve for controlling fluidic communication between said sampling chamber and each of the connected vacuum source and the connected purging fluid source via said third port.

8. The apparatus of claim 1,
   wherein said first port connector is capable of fluidically connecting a fused silica lined fluid sample container to said first port.

9. An offline solid phase microextraction (SPME) sampling process comprising:
   providing an offline SPME sampling system comprising: a vacuum source; a purging fluid source; a hollow body surrounding a sampling chamber; a first port of said hollow body having a first port connector capable of fluidically connecting a fluid sample container to said first port and a first port valve for controlling fluidic communication between a connected fluid sample container and said sampling chamber; a second port of said hollow body having a septum capable of receiving a SPME needle/fiber therethrough for sampling said sampling chamber thereby; means for fluidically connecting said vacuum source and said purging fluid source to said hollow body; and valve means for controlling fluidic communication between said vacuum source and said sampling chamber and between said purging fluid source and said sampling chamber;
   capturing a fluid sample in the fluid sample container;
   connecting the fluid sample container to said first port;
   controlling said first port valve to release a portion of the fluid sample from the fluid sample container into the sampling chamber;
   inserting the SPME needle/fiber through the septum of the second port and SPME sampling the fluid sample in the sampling chamber;
   removing the SPME needle/fiber from the second port; and
   purging and flushing the fluid sample from the sampling chamber.

10. An offline solid phase microextraction (SPME) sampling process comprising:
    providing an offline SPME sampling system comprising: a hollow body surrounding a sampling chamber; a first port of said hollow body having a first port connector capable of interchangeably fluidically connecting a fluid sample container, a vacuum source, and a purging gas source to said first port, and a first port valve for interchangeably controlling fluidic communication between said sampling chamber and a fluid sample container, a vacuum source, and a purging gas source; a second port of said hollow body having a septum capable of receiving a SPME needle/fiber therethrough for sampling said sampling chamber thereby;

capturing a fluid sample in the fluid sample container;

fluidically connecting the fluid sample container to said first port;

controlling said first port valve to release a portion of the fluid sample from the fluid sample container into the sampling chamber;

inserting the SPME needle/fiber through the septum of the second port and SPME sampling the fluid sample in the sampling chamber;

removing the SPME needle/fiber from the second port;

disconnecting the fluid sample container form from said first port fluidically connecting said first port to the purging gas source and the vacuum source; and purging and flushing the fluid sample from the sampling chamber.

11. An offline solid phase microextraction (SPME) sampling system, comprising:

a vacuum source;

a purging fluid source;

a hollow body surrounding a sampling chamber;

a first port of said hollow body having a first port connector adapted to physically and fluidically interconnect an access port of a fluid sample container to said first port so as to enable controlled fluidic communication with said sampling chamber;

a second port of said hollow body having a septum capable of being pierced by a SPME needle/fiber therethrough for sampling said sampling chamber thereby;

means for fluidically connecting said vacuum source and said purging fluid source to said hollow body; and valve means for controlling fluidic communication between said vacuum source and said sampling chamber and between said purging fluid source and said sampling chamber.

12. The system of claim 11, wherein said first port has a first port valve for controlling the fluidic communication between the connected fluid sample container and said sampling chamber.

13. The system of claim 11, wherein said first port connector is capable of fluidically connecting a fluid sample container of a type having an integrated valve for controlling the fluidic communication between the connected fluid sample container and said sampling chamber.

14. The system of claim 11, wherein said means for fluidically connecting and said valve means for controlling fluidic communication first port are integrated as part of said first port connector so as to interchangeably enable fluidic communication between said sampling chamber and each of said fluid sample container, the vacuum source, and the purging gas source.

15. The system of claim 11, further comprising third and fourth ports of said hollow body, and wherein said means for fluidically connecting comprises a third port connector capable of fluidically connecting the vacuum source to said third port, and a fourth port connector capable of fluidically connecting the purging fluid source to said fourth port; and said valve means comprises a third port valve for controlling fluidic communication between the connected vacuum source and said sampling chamber via said third port, and a fourth port valve for controlling fluidic communication between the connected purging fluid source and said sampling chamber via said fourth port.

16. system of claim 15, wherein said third port and said fourth port are on opposite sides of said hollow body.

17. The system of claim 11, further comprising a third port of said hollow body, and wherein said means for fluidically connecting comprises a third port connector capable of fluidically connecting the vacuum source and the purging fluid source to said third port; and said valve means comprises a third port valve for controlling fluidic communication between said sampling chamber and each of the connected vacuum source and the connected purging fluid source via said third port.

18. The system of claim 11, wherein said first port connector is capable of fluidically connecting a fused silica lined fluid sample container to said first port.

19. The system of claim 11, wherein the purging fluid source is a purging gas source.

20. The system of claim 19, wherein the purging gas of the purging gas source is nitrogen gas.

21. An offline solid phase microextraction (SPME) sampling process comprising:

providing an offline SPME sampling system comprising: a vacuum source; a purging fluid source; a hollow body surrounding a sampling chamber; a first port of said hollow body having a first port connector capable of fluidically connecting a fluid sample container to said first port said fluid sample container having an integrated valve for controlling the fluidic communication between said connected fluid sample container and said sampling chamber; a second port of said hollow body having a septum capable of receiving a SPMIE needle/fiber therethrough for sampling said sampling chamber thereby; means for fluidically connecting said vacuum source and said purging fluid source to said hollow body; and valve means for controlling fluidic communication between said vacuum source and said sampling chamber and between said purging fluid source and said sampling chamber;

capturing a fluid sample in the fluid sample container having the integrated valve;

connecting the fluid sample container to said first port;

controlling the integrated valve of said connected fluid sample container to release a portion of the fluid sample therefrom and into the sampling chamber;

inserting a SPME needle/fiber through the septum of the second port and SPME sampling the fluid sample in the sampling chamber;

removing the SPME needle/fiber from the second port; and purging and flushing the fluid sample from the sampling chamber.

22. The process of claim 21,
wherein the step of capturing the fluid sample comprises capturing the fluid sample in a fused silica lined fluid sample container.

23. The process of claim 22,
further comprising repeating the steps of controlling, inserting, removing, and purging and flushing at least once whereby multiple SPME samplings may be enabled using a single captured fluid sample.

24. The process of claim 21,
wherein the step of capturing the fluid sample includes capturing a headspace sample.

25. The process of claim 24,
wherein the step of purging and flushing includes using nitrogen gas to purge and flush the headspace sample from the sampling chamber.

* * * * *